United States Patent
Yu et al.

(10) Patent No.: US 7,449,593 B2
(45) Date of Patent: Nov. 11, 2008

(54) SILICON-CONTAINED ANTHRACENE COMPOUND FOR ORGANIC ELECTROLUMINESCENT DEVICE

(75) Inventors: Chen-Ping Yu, Hsin-Chu (TW);
Chia-Liang Tai, Hsin-Chu (TW);
Fan-Hsiu Chang, Hsin-Chu (TW)

(73) Assignee: Au Optronics Corporation, Hsin-Chu (TW)

( * ) Notice: Subject to any disclaimer, the term of this patent is extended or adjusted under 35 U.S.C. 154(b) by 0 days.

(21) Appl. No.: 11/693,266

(22) Filed: Mar. 29, 2007

(65) Prior Publication Data

US 2007/0173658 A1    Jul. 26, 2007

Related U.S. Application Data

(62) Division of application No. 11/179,573, filed on Jul. 13, 2005, now abandoned.

(30) Foreign Application Priority Data

Apr. 8, 2005    (TW) .................. 94111260

(51) Int. Cl.
*C07F 7/08* (2006.01)

(52) U.S. Cl. ........................................ 556/465

(58) Field of Classification Search ............ 556/400
See application file for complete search history.

(56) References Cited

FOREIGN PATENT DOCUMENTS

EP            1491609 A2  *  12/2004

OTHER PUBLICATIONS

Marcinow, Z.; Clawson, D.K.; Rabideau, P.W. Silicon-modified Birch reduction and reductive alkylation of polynuclear aromatics Tetrahedron (1989), 45 (17), 5441-8. (Abstract enclosed).*

* cited by examiner

*Primary Examiner*—Samuel A Barts
(74) *Attorney, Agent, or Firm*—Rosenberg, Klein & Lee

(57) ABSTRACT

This invention is about anthracene, at least one having silyl substituted group on ring 9 and 10, the anthracene can be a organic light emitting diodes (OLED) material and used for organic electroluminescent device.

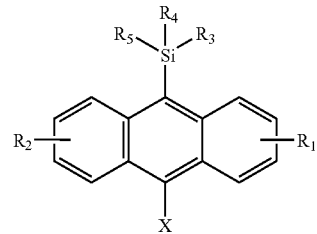

wherein X is an triarylsilyl group having 6 to 20 carbon atoms, an trialkylsilyl group having 1 to 12 carbon atoms, a substituted or unsubstituted aryl group having 6 to 20 carbon atoms, a substituted or unsubstituted heteroaryl group having 2 to 20 carbon atoms, or a substituted or unsubstituted alkyl group having 1 to 12 carbon atoms. $R_1$ and $R_2$ is independently a hydrogen, halogen, or a substituted or unsubstituted alkyl group having 1 to 12 carbon atoms. $R_3$ to $R_5$ is independently a substituted or unsubstituted aryl group having 6 to 20 carbon atoms, or a substituted or unsubstituted alkyl group having 1 to 12 carbon atoms.

2 Claims, 4 Drawing Sheets

SILICON-CONTAINED ANTHRACENE COMPOUND FOR ORGANIC ELECTROLUMINESCENT DEVICE

RELATED CASES

This application is a Divisional patent application of co-pending application Ser. No. 11/179,573, filed 13 Jul. 2005.

FIELD OF THE INVENTION

This invention relates to anthracene compound, particular on the position 9 and 10, and at least one having a substituted silyl group, the anthracene compound can be an organic light emitting diode (OLED) material and used for organic electroluminescent device.

BACKGROUND OF THE INVENTION

In recent years, the organic electroluminescent device having high efficiency and fluorescent dyes, can be used for the flat panel displays to bring this technology commercialization. In various types of flat panel displays, since an OLED, being developed later than a liquid crystal display (LCD), has many beneficial characteristics, such as a spontaneous light source, a wide viewing angle, high response velocity, high brightness, strong contrast, small thickness, power saving, and a wide operating temperature, the OLED has been used extensively in small and medium scale portable display fields.

The emitting layer is between the metal cathode and transparent anode in the organic electroluminescent device. When a DC voltage is applied to the OLED structure, electrons in the cathode and holes in the transparent conductive layer will be injected into the emitting layer through the electron transport layer and the hole transport layer respectively. Due to the potential difference incurred from the external electrical field, electrons and holes will move in the emitting layer and recombine as excitions. When the excitions come back to the ground state by way of releasing energy, the quantum efficiency is released in a form of photons to emit light downwards through the transparent anode. This is the organic electroluminescent principle.

For example, in U.S. Pat. No. 6,465,115 disclosed anthracene compound on the hole transport layer, which on position 9 and 10 having aryl group, the structure as following:

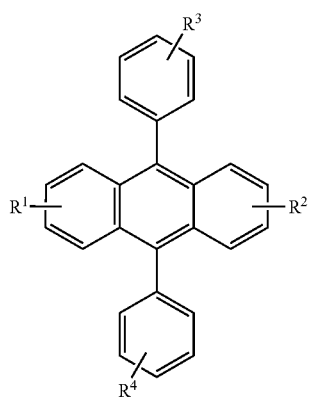

wherein substituents $R^1$ to $R^4$ are each individually hydrogen, or alkyl of from 1 to 24 carbon atoms; aryl or substituted aryl of from 5 to 20 carbon atoms; or heteroaryl or substituted of from 5 to 24 carbon atoms; or fluorine, chlorine, bromine; or cyano group.

In U.S. Pat. No. 5,759,444 also disclosed anthracene compound, the structure as following:

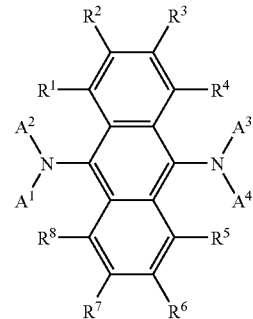

wherein each of $A^1$ to $A^4$ are a substituted or unsubstituted aryl group having 6 to 16 carbon atoms, and each of $R^1$ to $R^8$ are a hydrogen atom independently, a halogen atom, a substituted or unsubstituted alkoxy group, a substituted or unsubstituted aryl groups or a substituted or unsubstituted amino group.

In U.S. Pat. No. 6,310,231 disclosed silane compounds as a constituent material of luminescent device are described, which are represented by following formula:

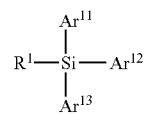

wherein $R^1$ represents an alkyl group, an aryl group, a heteroaryl group or an alkynyl group, and each of $Ar^{11}$, $Ar^{12}$, and $Ar^{13}$ represent a heteroaryl group.

Though the prior investigations described the organic light emitting diode, it is very important to make new and efficient organic EL materials to improve the spontaneous light source, a wide viewing angle, high response velocity, high brightness, strong contrast, small thickness, power saving, and a wide operating temperature in the organic electroluminescent device.

SUMMARY OF THE INVENTION

This invention provides an organic light emitting diode (OLED) material, which at least one having a substituted silyl group on the position 9 and 10 of the anthracene compound, said the anthracence compound represented by the following formula:

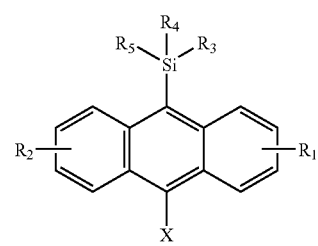

(A)

In the compound (A), X represents a substituted silyl group (more preferably triphenylsilyl group), a trialkylsilyl group having 1 to 20 carbon atoms (more preferably trimethylsilyl group, triethylsilyl group, or tripropylsilyl group, particularly preferably trimethylsilyl group), a substituted or unsubstituted aryl group having 6 to 20 carbon atoms (more preferably benzyl group, 2-methylbenzyl group, 3-methylbenzyl group, 4-methylbenzyl group, 4-ethylbenzyl group, biphenyl group, 4-methylbiphenyl group, 4-ethylbiphenyl group, 4-cyclohexylbiphenyl group, triphenyl group, naphthyl group, 5-methylnaphthyl group, anthryl group, or pyrenyl group, particularly preferably benzyl group, naphthyl group, biphenyl group, triphenyl group, or pyrenyl group etc.), a substituted or unsubstituted heteroaryl group having 2 to 20 carbon atoms (more preferably furanyl group, pyrrolyl group, pyridinyl group, pyrimidinyl group, pyranyl group, thiophenyl group, thiopyranyl, thiazolyl group, imidazolyl group, carbazole group, triazinyl group, quinolinyl group, particularly preferably pyridinyl group, carbazole group, or quinolinyl group), or a substituted or unsubstituted alkyl group having 1 to 12 carbon atoms (more preferably methyl, ethyl, propyl, or butyl).

In the compound (A), each $R^1$ and $R^2$ represent hydrogen, halogen, or a substituted or unsubstituted alkyl group having 1 to 20 carbon atoms (more preferably hydrogen, a substituted or unsubstituted alkyl group having 1 to 4 carbon atoms, fluorine, chlorine, or bromine, particularly preferably hydrogen, methyl group, ethyl group, propyl group, butyl group, fluorine, chlorine, or bromine), wherein $R^1$ and $R^2$ can be the same or not the same.

In the compound (A), each $R^3$, $R^4$, and $R^5$ represent a substituted or unsubstituted aryl group having 6 to 20 carbon atoms (more preferably benzyl group, 2-methylbenzyl group, 3-methylbenzyl group, 4-methylbenzyl group, 4-ethylbenzyl group, biphenyl group, 4-methylbiphenyl group, 4-ethylbiphenyl group, 4-cyclohexylbiphenyl group, triphenyl group, naphthyl group, 5-methylnaphthyl group, anthryl group, or pyrenyl group, particularly preferably benzyl group, naphthyl group, biphenyl group, triphenyl group, or pyrenyl group etc.), or a substituted or unsubstituted alkyl group having 1 to 12 carbon atoms (more preferably a substituted or unsubstituted alkyl group having 1 to 4 carbon atoms, particularly preferably methyl group, ethyl group, propyl group, or butyl group), wherein $R^1$ and $R^2$ can be the same or not the same.

According to the above anthracene compound (A), there are some compounds but not limited:

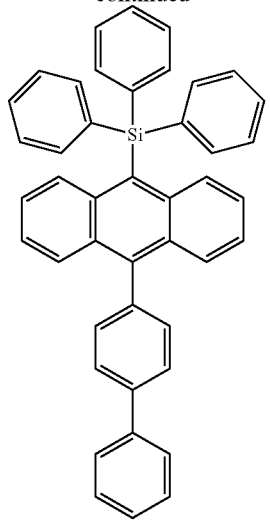

-continued

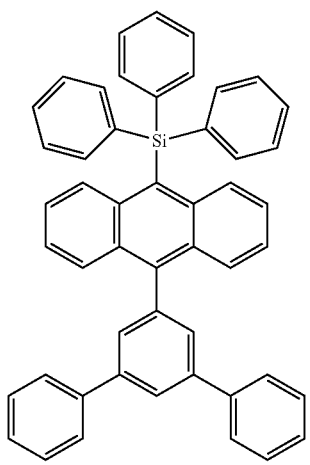

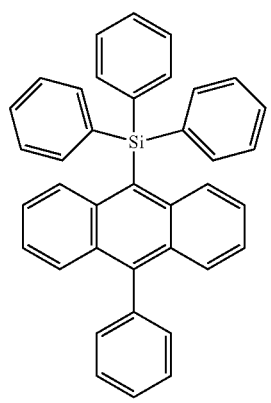

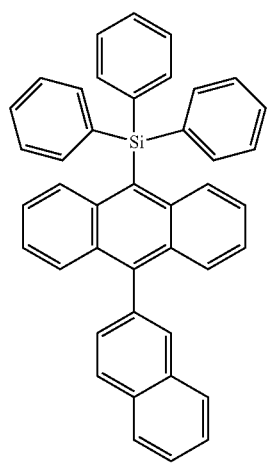

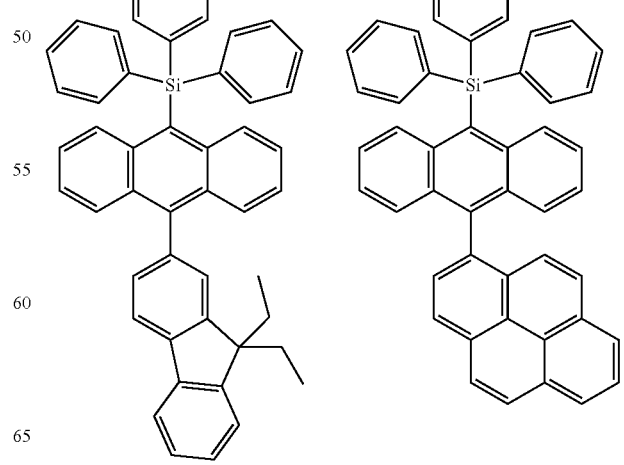

-continued

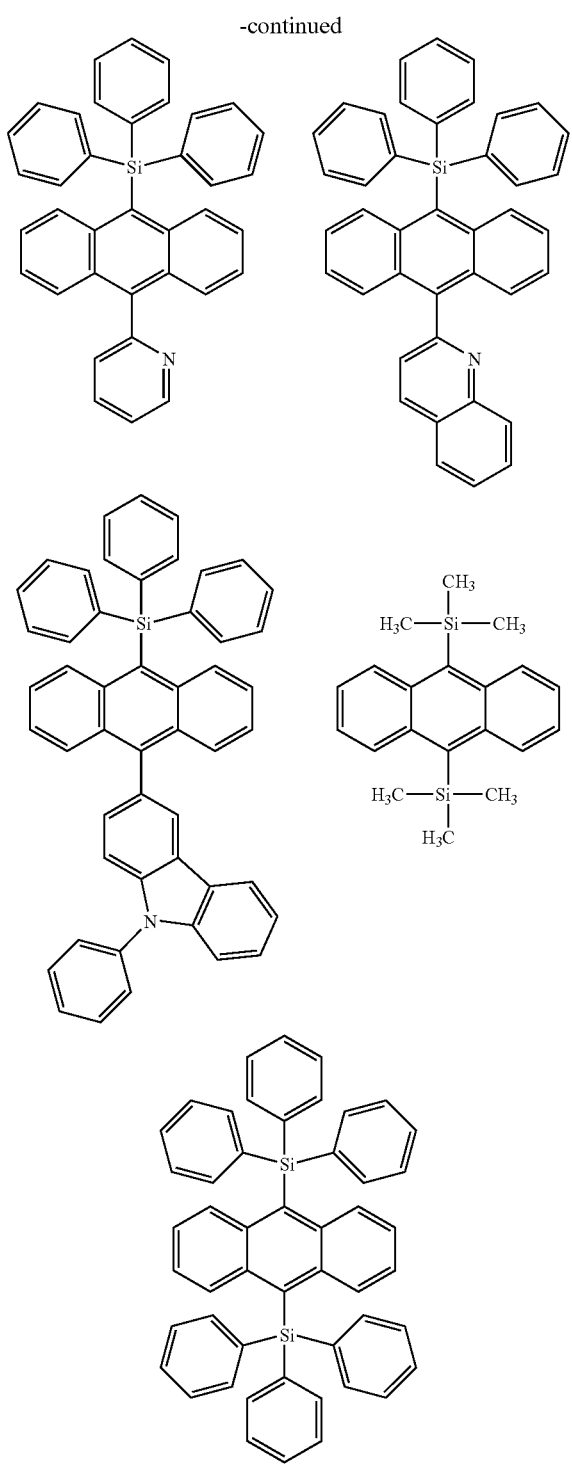

The invention also represents an organic electroluminescent device, which comprising:

a substrate;

a first electrode layer, which is on the substrate;

an organic layer, which is on the first electrode, and the organic layer including the anthracene compound (A) of mention above; and a second electrode layer, which is on the organic layer.

The substrate more preferably glass substrate, the first electrode layer more preferably a transparent conductive material, perfect preferably indium tin oxide film, the organic layer more preferably including a hole injection layer, a hole transport layer, a light emitting layer, a electron transport layer and a electron injection layer, wherein, the anthracene compound (A) is in the light emitting layer; the second electrode layer is more preferably a metal layer, perfect preferably Aluminum in the organic electroluminescent device.

Typical organic emitting materials were formed of a conjugated organic host material and a conjugated organic activating agent having condensed benzene rings. However, for the production of full color OLED display panel, it is necessary to have efficient red, green and blue (RGB) EL materials with proper chromaticity and sufficient luminance efficiency. The guest-host doped system offers a ready avenue for achieving such an objective, mainly because doping an emissive dopant of high luminescent property into a host can raise the efficiency of radiative recombination. This application also has dopant in the emissive layer, such as BDM. etc.

DETAILED DESCRIPTION OF THE PREFERRED EMBODIMENTS

Synthesis of Anthracene Compound

EXAMPLE 1

Synthesis of 9-bromo-10-triphenysilyl anthracene

Figure 1:
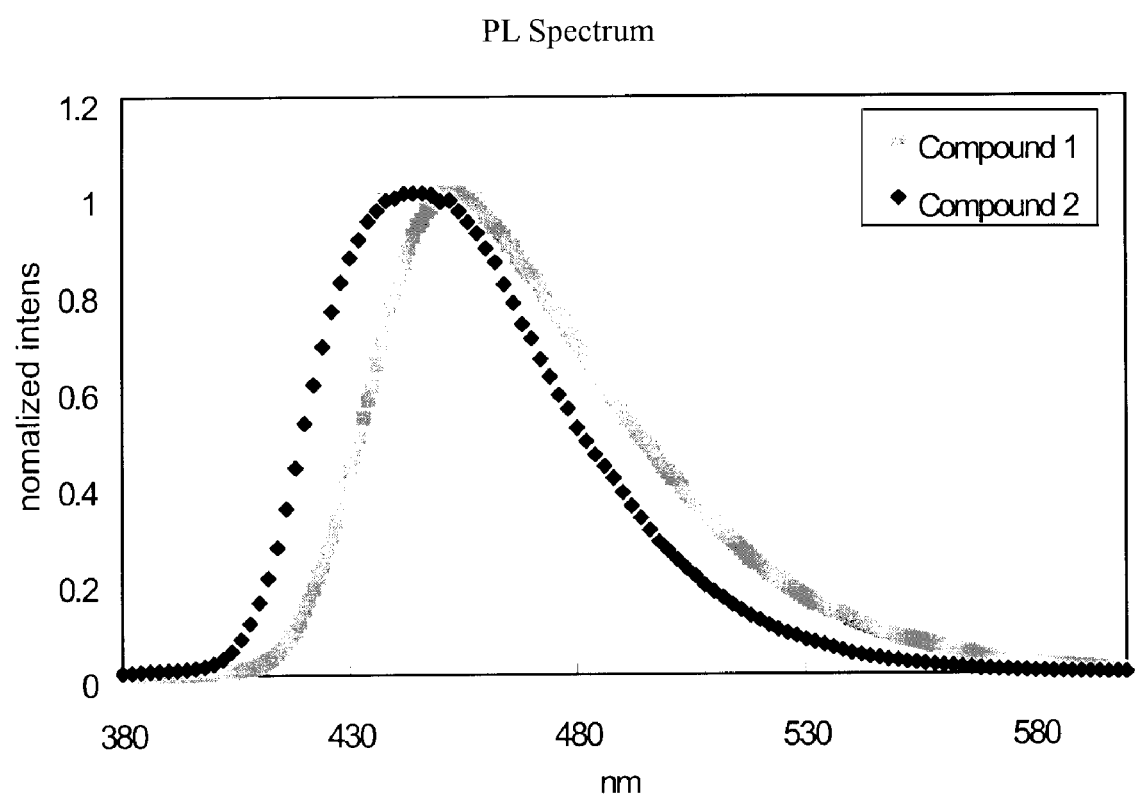
FIG. 1 shows the PL intensity in different waves about compound (1) and compound (2)

In a nitrogen atmosphere, 12 g (35.7 mmol) of 9,10-dibromoanthracene, and 300 ml of tetrahydrofuran (THF) were added to a round-bottom flask. Next, 14.4 ml (35.7 mmol, 2.5M) of n-butyl lithium was added dropwise slowly into the round-bottom flask at −78° C. After mixing and reacting for 30 min, 12 g (40.7 mmol) triphenylsilyl chloride with 50 ml THF were added dropwise slowly into the round-bottom flask at −78° C. After reacting at room temperature for 24 hours, the resulting mixture was subjected to extraction with a mixed solvent (ethyl acetate:$H_2O$), dried over anhydrous $MgSO_4$, filtered, and condensed, then the crude product was purified by column chromatography (n-hexane/acetyl acetate=15/1), A 9.0 g of pure 9-bromo-10-triphenysilyl anthracene was collected.

EXAMPLE 2

Synthesis of 9, 10-di-triphenysilyl anthracene (Compound 1)

In a nitrogen atmosphere, 9 g (17.5 mmol) of 9-bromo-10-triphenysily anthracene, and 200 ml of tetrahydrofuran (THF) were added to a round-bottom flask. Next, 7.7 ml (19.3 mmol, 2.5M) of n-butyl lithium was added dropwise slowly into the round-bottom flask at −780° C. After mixing and reacting for 30 min, 6.2 g (21.2 mmol) triphenylsilyl chloride with 50 ml THF added dropwise slowly into the round-bottom flask at −780° C. After reacting at room temperature for 24 hours, the resulting mixture was subjected to extraction with a mixed solvent (ethyl acetate:$H^{20}$), dried over anhydrous $MgSO^{4}$, filtered, and condensed, then the crude product was purified by column chromatography (n-hexane/acetyl acetate 15/1), a 4.2 g of pure 9,10-di-triphenysilyl anthracene was collected, the reaction was following:

EXAMPLE 3

Synthesis of 9-(2-naphthyl)-10-triphenysilyl anthracene (Compound 2)

9-bromo-10-triphenysilyl anthracene (4 g, 7.8 mmol), 2-naphthylboronic acid (1.6 g, 9.4 mmol) and $K_2CO_3$ (1.5 g, 15.6 mmol) were dissolved in the solvent mixture of 50 mL ethylene glycol dimethyl ether and 75 mL water. The stirred solution was added tetrakis (triphenylphosphine) palladium (0) and the mixture refluxed under N2 for 16 hours. The reaction mixture was cooled and the water extracted with acetyl acetate three times. The combined organic phase was washed with portions of brine. The organic layer was then dried with $MgSO_4$, filtered, and evaporated of solvent. The crude material was purified by column chromatography (n-hexane/acetyl acetate=10/1) to give 9-(2-naphthyl)-10-triphenysilyl anthracene (Compound 2), the reaction was following:

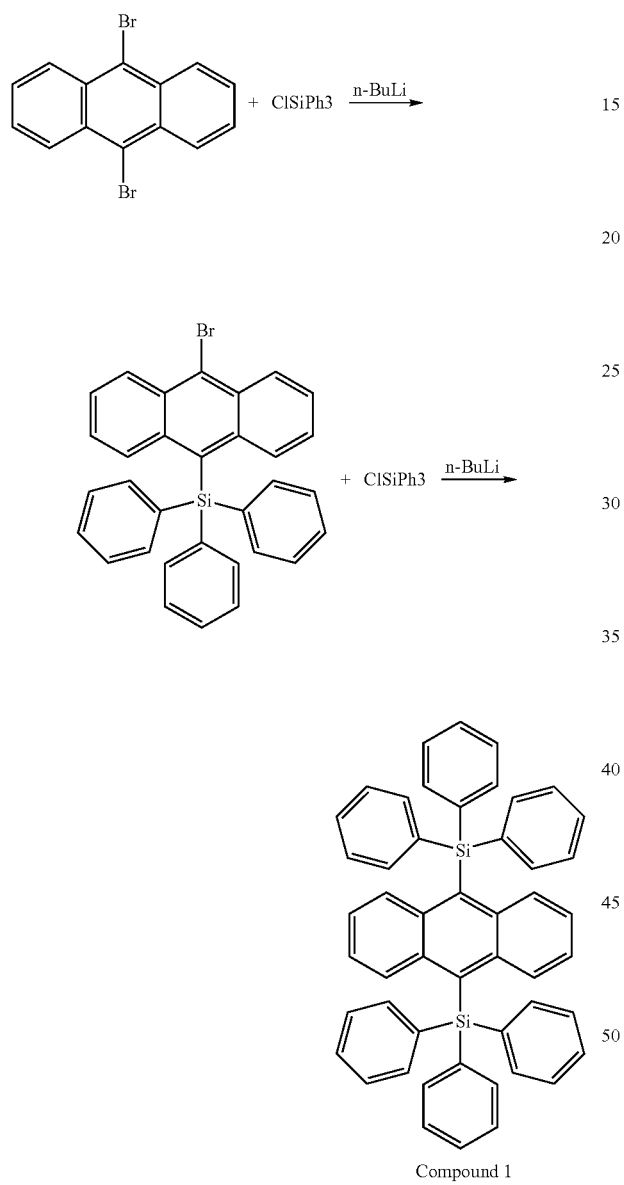

Compound 1

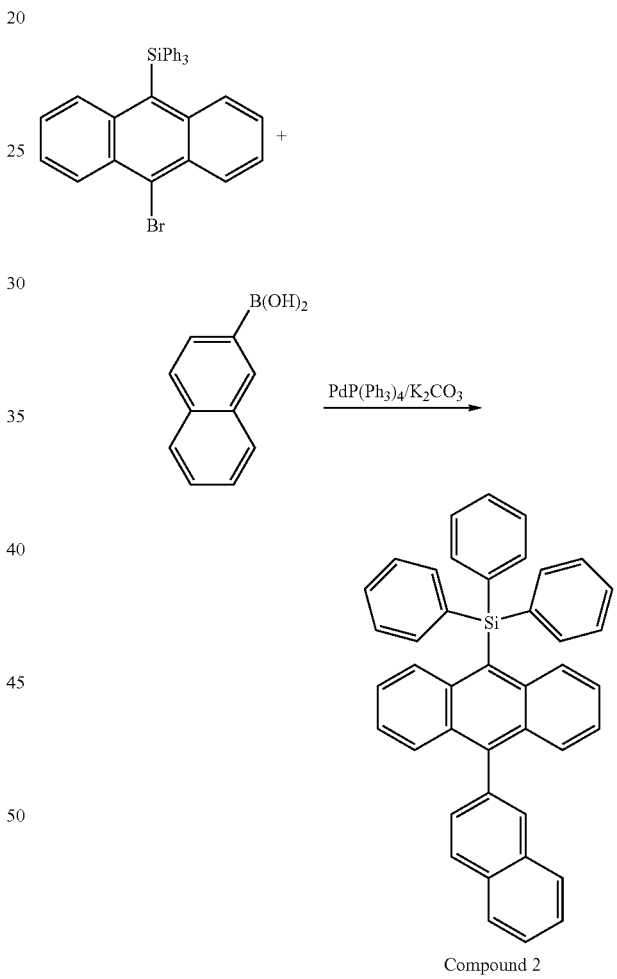

Compound 2

TABLE 1

| | Device Characteristics of Examples | | | | | | |
|---|---|---|---|---|---|---|---|
| | emitting layer material | | Operation Voltage (V) | Brightness (cd/m$^2$) | CIE chromaticity coordinates (X axis) | CIE chromaticity coordinates (Y axis) | Efficiency (cd/A) |
| Example | Host | Dopant | | | | | |
| Example 4*[1] | anthracene compound (1) | BDM*[2] | 8.5 | 1000 | 0.15 | 0.13 | 2.1 |

TABLE 1-continued

| | | | | | | | |
|---|---|---|---|---|---|---|---|
| Example 5*[1] | ADN*[3] | anthracene compound (1) | 7.0 | 1000 | 0.20 | 0.23 | 1.7 |
| Example 6*[1] | anthracene compound (2) | BDM*[2] | 8.5 | 1000 | 0.14 | 0.13 | 2.4 |
| Compare Example 1*[1] | ADN*[3] | BDM*[2] | 7.1 | 1000 | 0.15 | 0.14 | 2.6 |

*[1]The hole injection layer is consisted of 2T-NATA (4,4',4''-tri(N-(2-naphthyl)-N-aniline)-triphenyl amine); the hole transport layer is consisted of NPB (N,N'-di-1-naphthyl-N,N'-diphenyl-1,1'-biphenyl-1,1'-biphenyl-4,4'-diamine); the electron transport layer is consisted of Alq$_3$ (tris (8-hydroxyquinoline) aluminum).
*[2]BDM:

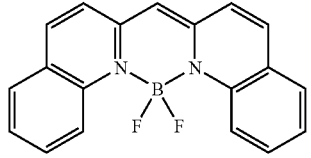

*[3]ADN:

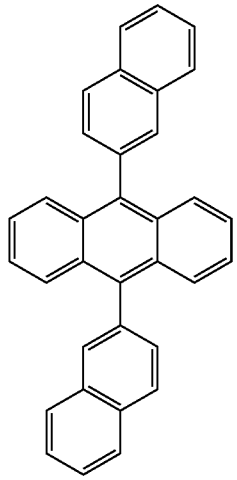

From table 1, in the present invention, the host material of emitting layer being the anthracene compound, as Example 4 and 6, the CIE chromaticity coordinates (Y axis) from 0.14 to 0.13. The organic electroluminescent element approaches to blue light. Furthermore, this invention also can be dopant, as Example 5.

Figure 2:
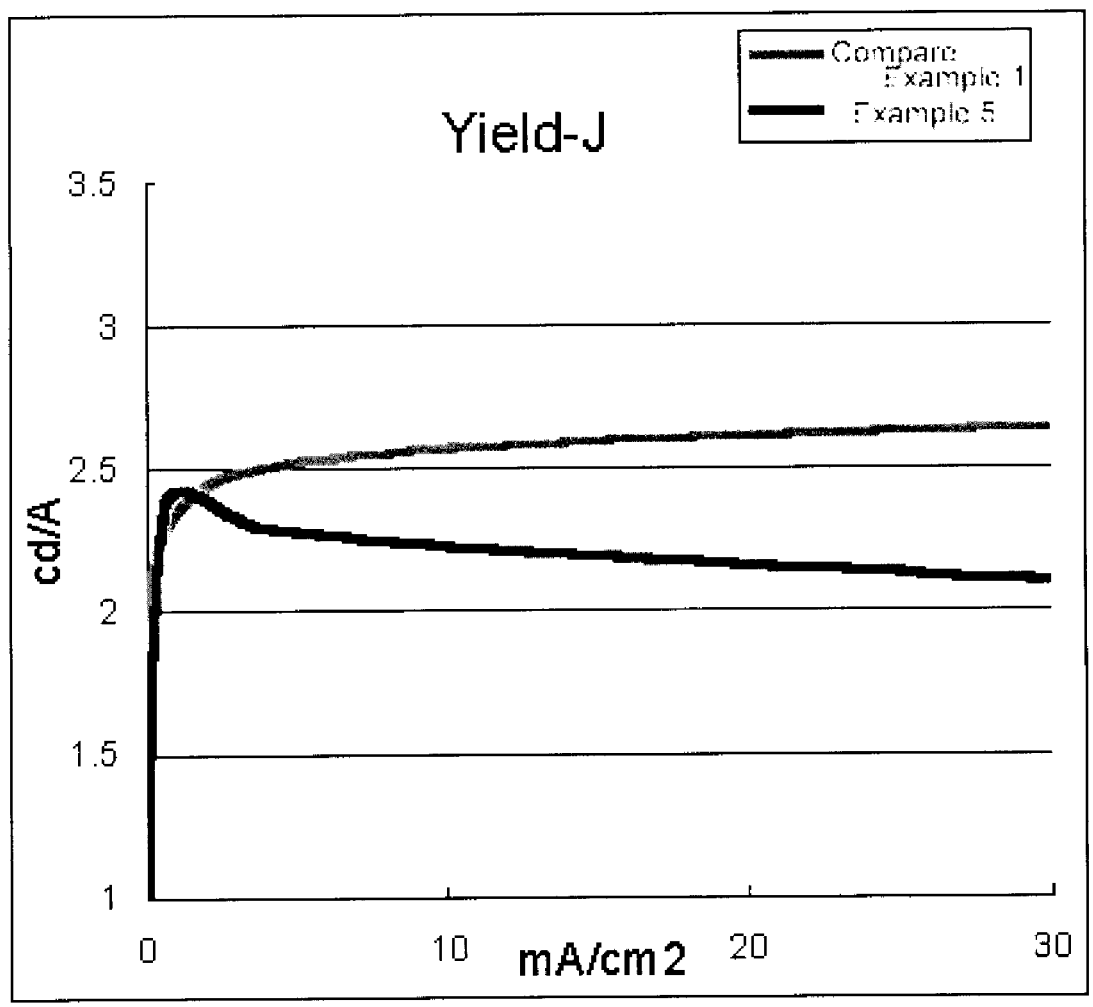
FIG. 2 shows the efficiency of organic light emitting diode material in example 5 and compare example 1.
Figure 3A:
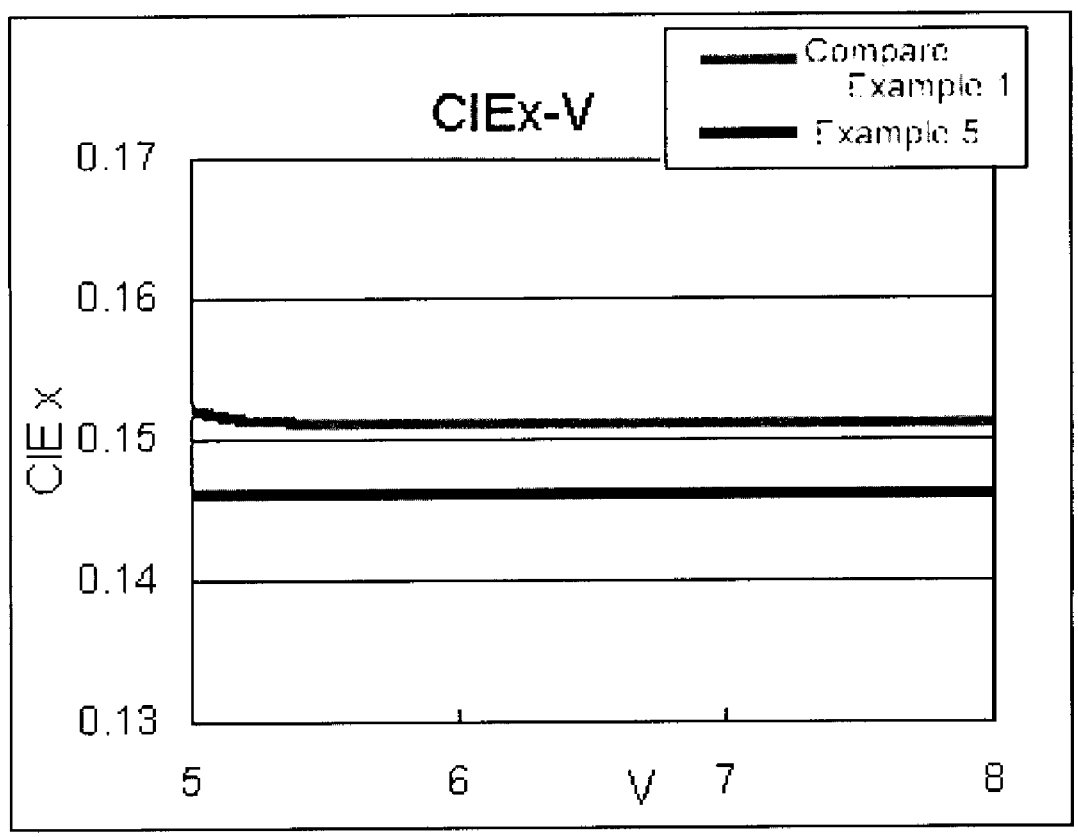
FIG. 3(a) and FIG. 3(b) show the different of organic light emitting diode material in the CIE chromaticity coordinates between example 5 and compare example 1, wherein both the horizontal axis represent voltage, the vertical axis represents CIEx in FIG. 3(a), and the vertical axis represents CIEy in FIG. 3(b).
Figure 3B:
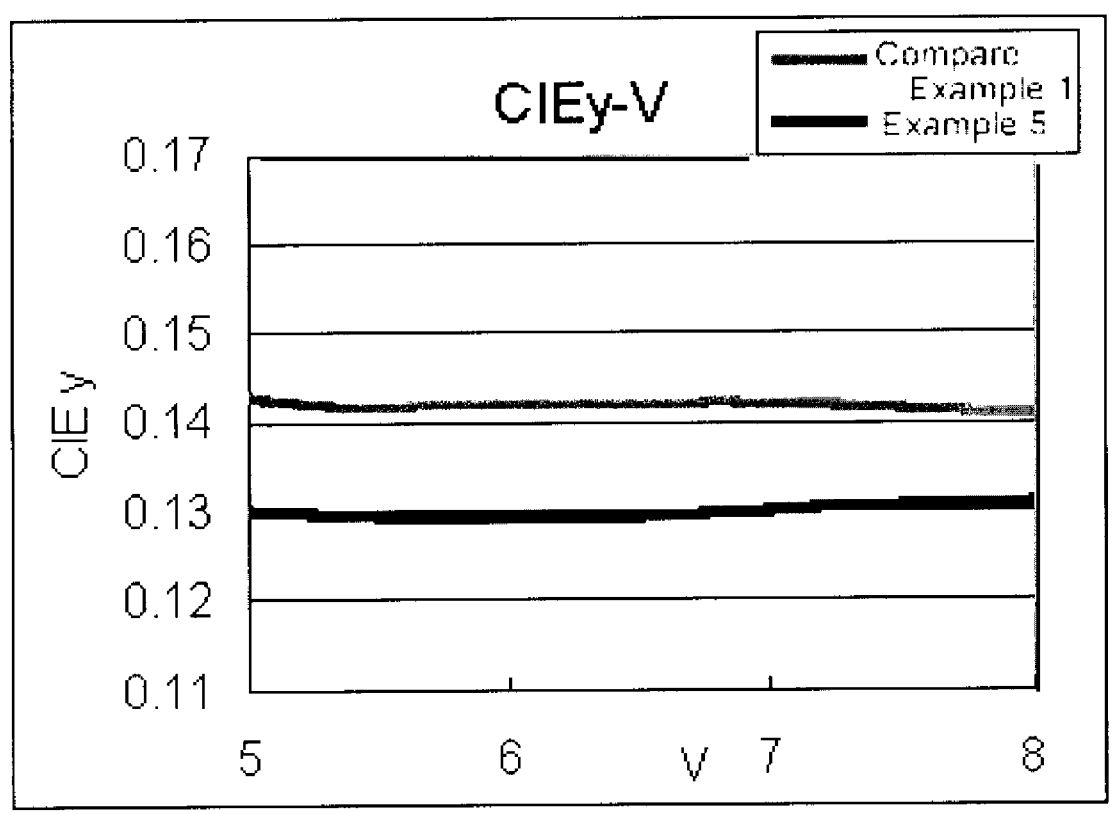

Comparing the Example 5 with the Example 1, it is known the efficiency and the color gamut of the present compound (Example 5) better than the Example 1 from FIG. 2, FIG. 3(a) and FIG. 3(b).

Those skilled in the art will readily observe that numerous modifications and alterations of the device and method may be made while relating the teachings of the invention. Accordingly, the above disclosure should be construed as limited only by the meters and bounds of appended claims.

What is claimed is:

1. An anthracene compound, represented by the following formula:

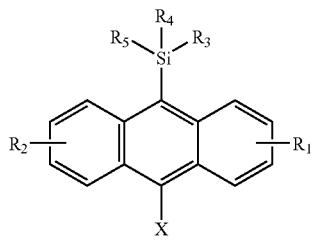

wherein X represents a substituted or unsubsituted aryl group having 6 to 20 carbon atoms, a substituted or unsubstituted heteroaryl group having 2 to 20 carbon atoms, or a substituted or unsubstituted alkyl group having 1 to 20 carbon atoms;

$R_2$ represent hydrogen, halogen, or a substituted or unsubstituted alkyl group having 1 to 20 carbon atoms, $R_1$ represents the fluorine, the chlorine, or the bromine, $R_1$ and $R_2$ can be the same or not the same; and each $R_3$, $R_4$, and $R_5$ represent a substituted or unsubstituted aryl group having 6 to 20 carbon atoms, or a substituted or unsubstituted alkyl group having 1 to 12 carbon atoms, $R_3$, $R_4$, and $R_5$ can be the same or not the same.

2. An anthracene compound, represented by the following formula:

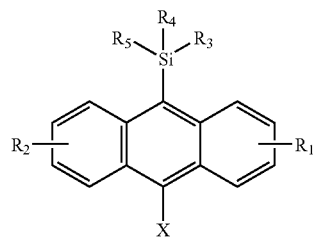

wherein X represents a substituted or unsubsituted aryl group having 6 to 20 carbon atoms, a substituted or unsubstituted heteroaryl group having 2 to 20 carbon atoms, or a substituted or unsubstituted alkyl group having 1 to 20 carbon atoms;

$R_1$ represent hydrogen, halogen, or a substituted or unsubstituted alkyl group having 1 to 20 carbon atoms, $R_2$ represents the fluorine, the chlorine, or the bromine, $R_1$ and $R_2$ can be the same or not the same; and each $R_3$, $R_4$, and $R_5$ represent a substituted or unsubstituted aryl group having 6 to 20 carbon atoms, or a substituted or unsubstituted alkyl group having 1 to 12 carbon atoms, $R_3$, $R_4$, and $R_5$ can be the same or not the same.

* * * * *